United States Patent [19]

Hilton

[11] Patent Number: 4,615,806
[45] Date of Patent: Oct. 7, 1986

[54] REMOVAL OF IODIDE COMPOUNDS FROM NON-AQUEOUS ORGANIC MEDIA

[75] Inventor: Charles B. Hilton, Corpus Christi, Tex.

[73] Assignee: Celanese Corporation, New York, N.Y.

[21] Appl. No.: 708,992

[22] Filed: Mar. 7, 1985

[51] Int. Cl.[4] .......................................... B01D 15/04
[52] U.S. Cl. ..................................... 210/690; 562/608
[58] Field of Search ............... 210/663, 668, 669, 683, 210/690, 692, 694, 902, 908; 562/608

[56] References Cited

U.S. PATENT DOCUMENTS

| | | |
|---|---|---|
| 1,843,354 | 2/1932 | Behrman . |
| 2,945,746 | 7/1960 | Shaw ................................. 210/683 |
| 3,658,467 | 4/1972 | Maeck ................................. 55/71 |
| 3,838,554 | 10/1974 | Wilhelm et al. .................... 55/71 |
| 3,943,229 | 3/1976 | Keener et al. ...................... 423/240 |
| 4,008,131 | 2/1977 | Price .................................. 562/608 |
| 4,088,737 | 5/1978 | Thomas et al. .................... 423/240 |
| 4,238,294 | 12/1980 | Takeuchi et al. .................. 203/72 |
| 4,451,375 | 5/1984 | Grinstead ........................... 210/683 |

FOREIGN PATENT DOCUMENTS 2645552 7/1977 Fed. Rep. of Germany .
48-37762 11/1973 Japan .

OTHER PUBLICATIONS

Hingorani et al., Chem Eng. World, 12(5) 59–60, 1977.
Donner et al. Kerntechnik, 14(1) 22–8 (1972).
J. Nucl. Sci. Technol., 9(4), 197, (1972).
Rohm and Haas Technical Bulletin, Amberlyst ® 15, 1978.
F. Cejnav, Jad. Energ., 18(6), 199 (1972).

Primary Examiner—Ivars Cintins
Attorney, Agent, or Firm—R. F. Green; D. R. Cassady

[57] ABSTRACT

The invention relates to a method for removing iodide compounds from a non-aqueous organic medium, such as acetic acid. The medium is contacted with a macroreticulated strong-acid cation exchange resin which is stable in the organic medium and has at least one percent of its active sites converted to the silver or mercury form.

7 Claims, No Drawings

REMOVAL OF IODIDE COMPOUNDS FROM NON-AQUEOUS ORGANIC MEDIA

BACKGROUND OF THE INVENTION

This invention relates generally to a method for removing iodide compounds from non-aqueous, organic media, such as acetic acid.

The present invention is concerned with the problem of removing iodide compounds which are present, typically in small quantities, in certain non-aqueous organic media. Of particular concern is the presence of small amounts of iodide compounds such as methyl iodide, sodium iodide, and hydrogen iodide, in acetic acid. Such iodide contamination can be of great concern to the users of the acetic acid as it may cause processing difficulties when the acetic acid is subjected to subsequent chemical conversion. The iodide compounds present in the acetic acid may also cause iodide contamination of any other material to which is added.

A need therefore exists for an economically reasonable, commercially acceptable method for the removal of iodide compounds from non-aqueous, organic media, such as acetic acid.

Heretofore certain approaches to the removal of iodide compounds from various aqueous and non-aqueous media have been undertaken. To the extent that the approaches discussed below have related to the removal of iodide compounds from non-aqueous, organic media, they have not found commercial acceptability for large scale industrial processes.

The use of ion-exchange resins to remove iodine and/or iodide compounds from certain liquid or gaseous streams has been taught with respect to certain specific ion-exchange resins. Thus, the use of a H-type strongly acidic cation-exchange resin, such as an $RSO_3H$-type, in a column (in combination with an anion-exchange resin with quaternary ammonium groups and a free-base type anion-exchange resin with ternary amine groups) to remove iodine and alkyl iodide from aqueous solutions or gases, is taught in Japanese Pat. No. 73 37,762 published Nov. 13, 1973.

U.S. Pat. No. 3,943,229 shows the use of certain cross-linked acrylic anion exchange resins to remove iodine and compounds thereof from gaseous streams. In U.S. Pat. No. 4,238,294, various ion-exchange resins are employed to remove heavy metal ions and in some instances halogen values, from certain carboxylic acid solutions, principally through the use of strongly basic anion exchange resins.

Likewise, macroporous styrene-divinylbenzene copolymers have been shown to be effective in absorbing methyl iodide from air, as taught in F. Cejnav,*Jad. Energ.*, 18(6), 199 (1972).

The use of silver-impregnated supports has also been taught. A gel-type ion exchange resin impregnated with silver by soaking in a silver-nitrate solution has been indicated to be useful in absorbing iodine and methyl iodide from an aqueous medium, as discussed in Hingorani et al, *Chem Eng. World*, 12(5) 59–60, 1977. Molecular sieves loaded with silver ions have also been indicated to be useful for the removal of methyl iodide from gaseous streams, as taught in Donner et al, *Kerntechnik*, 14(1), 22–8 (1972) and U.S. Pat. No. 3,658,467. Likewise, a column of silica impregnated with silver nitrate has been stated to be effective in removing methyl iodide in the vapor phase, as shown in U.S. Pat. No. 3,838,554.

In U.S. Pat. No. 4,088,737 mention is made of the use of silver-exchanged zeolite to remove iodine from a waste gas stream and the subsequent regeneration of the zeolite by use of hydrogen to remove the iodine which is in turn absorbed onto a lead-exchanged zeolite.

Another means for removing methyl iodide in a vapor phase process is discussed in West German Pat. No. 2,645,552 wherein a ceramic material having a surface area of 5–250 $M^2$/g impregnated with mixtures of water and triethylenediamine is employed.

The use of carbonaceous materials to remove iodine or iodide compounds from aqueous solution has been known for a long period of time, and is discussed, for example, in U.S. Pat. No. 1,843,354. The removal of methyl iodide using charcoal with triethylenediamine is discussed in Bonhate et al, *Proc. Clean Air Conv.*, 114–119, 1972 and the use of activated charcoal impregnated with KSCN or $SnI_2$ is shown in *J. Nucl. Sci. Technol.*, 9(4), 197, (1972).

In a technical bulletin by Rohm and Haas dated September, 1978, Amberlyst ®15, a strongly acidic resin having a macroreticular porous structure, is shown to be used to remove ferric ion from glacial acetic acid. In the same bulletin, it is also stated that Amerlyst ®15 resin may be converted to any form such as sodium, potassium, and calcium by standard techniques employed in ordinary ion exchange processes.

SUMMARY OF THE INVENTION

In accordance with one aspect of the present invention there is provided a method for removing iodide compounds from a non-aqueous organic medium, comprising contacting the medium containing said iodide compounds with an ion exchange resin. The ion exchange resin is characterized in that it is a macroreticulated strong-acid cation exchange resin which is stable in the organic medium and has at least one percent of its active sites converted to the silver or mercury form. In one embodiment of the present invention, the non-aqueous organic medium is acetic acid.

In accordance with another aspect of the present invention there is provided a macroreticulated strong acid cation exchange resin having at least one percent of its active sites converted to the silver or mercury form.

DETAILED DESCRIPTION OF THE PREFERRED EMBODIMENTS

As discussed above, the present invention provides a method for removing iodide compounds from non-aqueous, organic media. Such media may therefore be organic acids, alcohols, ethers, esters, and the like. One such medium of particular importance is acetic acid. By the term "non-aqueous", it is simply meant that water is not present to any significant extent, and would therefore not typically be present in an amount significantly past its solubility in the organic medium which is being processed. When acetic acid is being processed in accordance with the present invention, for example, it usually has not more than about 0.15 percent, by weight, of water present.

The total amount of iodide compounds present in the non-aqueous, organic medium will, of course, vary depending upon the specific nature of the medium. The present process is broadly applicable for the removal of iodide compounds which are present in virtually any concentration in the organic medium. Thus, the present invention is applicable for the removal of iodide compounds from media in which the concentration of iodide compounds ranges from only trace amounts, less than 1 part per million ("ppm"), up to about the solubility limit of the iodide compounds in the particular medium.

When the present invention is applied to acetic acid, the total amount of iodide compounds present is usually from about 1 part per billion ("ppb") to about 100 ppb.

The specific nature of the iodide compounds which are removed by the present invention is also not critical. Typical of the iodide compounds which can be removed by the present invention are alkyl iodides, such as methyl iodide, hydrogen iodide, inorganic iodide salts, such as sodium iodide, and, to an extent, alpha-iodoaliphatic carboxylic acids.

Of particular significance is the fact that in the context of the present invention it has been discovered that hexyl iodide is present in some commercially produced acetic. It has also been discovered that hexyl iodide is particularly difficult to remove. A particularly significant aspect of the present invention is the ability of the method disclosed herein to remove hexyl iodide from acetic acid.

As previously indicated, the present invention employs an ion exchange resin which has been at least partially converted to the silver or mercury form. It is important in the practice of the present invention to use an ion exchange resin with suitable properties. The ion exchange resin should not be of the gel-type. As is known, gel-type polymers are characterized by the fact that their porosity essentially depends upon the volume increase which they exhibit upon exposure to a given solvent system. Ion exchange resins which depend essentially upon swelling for their porosity are not suitable for the practice of the present invention.

The ion exchange resins used in the present invention may thus be termed "non-gel-type" ion exchange resins. Such useful resins are typically considered to be macroreticular ion exchange resins and usually have pores considerably larger than those of the gel-type. However, the present invention is not limited to any specific pore-size of the ion-exchange resin. Usually the ion exchange resins used in the present invention have an average pore size from about 50 to about 1,000 angstroms. Preferably, the average pore size is from about 200 to about 700 angstroms.

The ion-exchange resin should also be of the type typically classified as a "strong acid" cation exchange resin. Preferably the resin is of the "RSO3H type." It is beyond the scope of the present invention to teach how to manufacture or otherwise characterize ion exchange resins, as such knowledge is already well known in that art. For the purposes of the present invention it is sufficient to characterize an ion exchange resin useful therein as being a strongly-acidic cation exchange resin of the non-gel type, and thus macroreticulated.

A preferred ion exchange resin for use in the practice of the present invention is a macroreticulated resin comprised of a sulfonated copolymer of styrene and divinyl benzene. The most preferred resin such as that available from Rohm and Haas under the trademark Amberlyst ®15, has the following properties:

| Appearance | Hard, dry, spherical particles |
| --- | --- |
| Typical particle size distribution percent retained on | |
| 16 mesh U.S. Standard Screens | 2-5 |
| −16 + 20 mesh U.S. Standard Screens | 20-30 |
| −20 + 30 mesh U.S. Standard Screens | 45-55 |
| −30 + 40 mesh U.S. Standard Screens | 15-25 |
| −40 + 50 mesh U.S. Standard Screens | 5-10 |
| Through 50 mesh, percent | 1.0 |
| Bulk density, lbs./cu. ft. | 38 (608 g/L) |
| Moisture, by weight | less than 1% |
| Percentage swelling from dry state to solvent-saturated state - | |
| hexane | 10-15 |
| toluene | 10-15 |
| ethylene dichloride | 15-20 |
| ethyl acetate | 30-40 |
| ethyl alcohol (95%) | 60-70 |
| water | 60-70 |
| Hydrogen ion concentration meq./g. dry | 4.7 |
| Surface Area, m$^2$/g. | 50 |
| Porosity, ml.pore/ml.bead | 0.36 |
| Average Pore Diameter, Angstroms | 240 |

A final characteristic of the resin when used to remove iodide compounds from non-aqueous, organic media, and one that is inherent in most ion exchange resins meeting the foregoing requirements, especially when the resin is specifically indicated to be designated for non-aqueous applications, is that the resin is stable in the organic medium from which the iodide compounds are to be removed. By the term "stable," it is meant that the resin will not chemically decompose, or change more than about 50 percent of its dry physical dimension upon being exposed to the organic medium containing the iodide compounds.

The ion exchange resin as indicated above, should be at least partially converted to the silver or mercury form. Conversion to the silver form is preferred.

The method of converting the ion exchange resin to the silver or mercury form is not critical. Any mercury or silver salt which has reasonable solubility in water or a suitable non-aqueous organic medium can be used. Silver acetate and silver nitrate are typical salts. The organic medium which may be used to load silver ions on the exchange resin may be, for example, acetic acid. When mercury is desired, rather than silver, a suitable salt is mecuric acetate.

The ion exchange resin is converted, to the desired degree, to the silver or mercury form, by simply contacting the resin with a solution of the desired silver or mercury salt for a sufficient length of time to allow for association of the metal ions with the resin.

The amount of silver or mercury associated with the resin is not critical and may be from as low as about 1 percent of the active acid sites to as high as 100 percent, converted to the silver or mercury form. Preferably about 25 percent to about 75 percent are converted to the silver or mercury form, and most preferably about 50 percent. As stated previously, the preferred metal is silver.

As some silver may be leached from the silver-treated ion exchange resin during conditions of actual use, it may be useful to have a bed of ion-exchange resin which has not been previously converted to the silver-form, placed downstream of the bed of silver-treated ion exchange resin. With respect to the processing steps, the non-aqueous organic medium which contains the iodide impurities is simply placed in contact with the silver-loaded ion exchange resin described above, using any suitable means. For example, the resin may be packed into a column by pouring slurries thereof into a column. The organic medium is then simply allowed to flow therethrough. Any other suitable means of placing the resin in contact with the organic medium may be employed.

When a packed column is used, the organic medium is usually allowed to flow therethrough at a predetermined rate. The particular rate used in any given instance will vary depending upon the properties of the organic medium, the particular resin, the degree and nature of the iodide compounds to be removed, and the percent of iodide compounds to be removed.

A typical flow rate, such as is used when acetic acid is to be purified, is from about 0.5 to about 20 bed volumes per hour ("BV/hr"). A bed volume is simply the volume of the resin bed. A flow rate of 1 BV/hr then means that a quantity of organic medium equal to the volume occupied by the resin bed passes through the resin bed in a one hour time period. Preferred flow rates are usually about 6 to about 10 BV/hr and the most preferred flow rate is usually about 8 BV/hr.

The temperature at which the iodide compound removal takes place is also not critical. Broadly, the method may be performed at any temperature from about the freezing point of the organic liquid to the decomposition temperature of the resin. As a practical matter, the temperature employed is usually from about 17° C. to about 100° C., typically from about 18° C. to about 50° C., and preferably under ambient conditions of about 20° C. to about 45° C.

In one embodiment of the present invention the non-aqueous organic medium is contacted with a carbonaceous material in addition to contacting the aforementioned ion exchange resin. Preferably, the carbonaceous material is used in a contacting step prior to the step of contacting the ion exchange resin. Although the aforementioned ion exchange resin is useful in removing iodide compounds, it is not very effective in removing iodine itself.

As discussed in U.S. Pat. No. 1,843,354, carbonaceous materials have been found to be effective absorbers of iodine. Carbonaceous materials listed therein include activated carbons, wood charcoals, bone char, lignite and the like. Preferably, activated carbon is used. It appears that activated carbons of the type usually identified as gas-phase carbons work best in removing iodine from such organics. Gas-phase activated carbons typically have surface areas on the order of 1,000 to 2,000 m$^2$/g. The most preferred activated carbon is one derived from coconut shells, such as is available under the designation Pittsburgh PCB 12×30 carbon.

Usually the non-aqueous organic medium is placed in contact with the carbonaceous material in the same manner as with the ion exchange resin, under the same or comparable conditions.

The invention will be further described by the following non-limiting examples.

EXAMPLE I (Comparative)

To demonstrate that the process disclosed in Japanese Pat. No. 73 37,762 is not very effective in removing iodide compounds from acetic acid, the following procedure was employed.

A 24 MM (ID) column was packed by pouring slurries of the desired column materials in acetic acid in the column, and draining the excess acid from the column. From bottom to top the column was packed with 20 ml of a free base ion exchanger (Amberlite ®IRA 45), 3 ml of activated carbon, 20 ml of a anion exchange resin with quaternary ammonium groups (Amberlite ®IRA 900), 3 ml of activated carbon, 20 ml of a strongly acidic cation exchange resin (Amberlyst ®15), and 12 ml of activated carbon.

Acetic acid (150 ml) was allowed to flow though the packed column until little color leaked from the column. A 50 ml portion of acetic acid containing 0.865 wt % methyl iodide (0.2 1 ml MeI/50 ml solution) was allowed to flow though the column at a flow rate of 12 ml/min and collected. Contact time was approximately 150 seconds.

The concentration of MeI in the treated sample was 0.26%, giving a maximum removal efficiency of 70% (dilution of the iodide containing sample with acetic acid left in the column after the wash results in some decrease in iodide concentration).

EXAMPLE II (Comparative)

To demonstrate that silver-charged gel-type resins are not very effective in removing iodide compounds from acetic acid, the following procedure was employed.

A 40 ml portion of hydrated Dowex ®50 W strong acid ion exchange resin was packed in a column and charged with silver ion by passing a solution of 8 g AgNO$_3$ in water through the column. Acetic acid was allowed to pass through the column, followed by a solution of 0.865% MeI in acetic acid, at a flow rate of 18 BV/hr (contact time of ~100 sec.). A maximum of 30% of the MeI was removed by the Ag-charged resin.

EXAMPLE III (Comparative)

To demonstrate that silver-exchanged zeolite is not effective in removing iodide compounds from acetic acid, the following procedure was employed.

A 50 ml portion of molecular sieve (1/16″ Linde 5APLTS) was mixed with 8.2 AgNO$_3$ in 50 ml acetic acid for about 30 minutes. The silver-exchanged zeolite was packed in a 50 ml buret. A solution of 0.865% methyl iodide in acetic acid was allowed to pass through the buret at a flow rate of 1 bed volume (50 ml) per hour (average contact time ~20 minutes). Silver leached continuously during the run. A yellowish percipitate (AgI) formed in the treated acetic acid indicating that some MeI passed through the buret. The treated acetic acid was not analyzed further.

EXAMPLE IV

A 30 ml portion of Amberlyst ®15 ion exchange resin was mixed with 100 ml water and 8 g AgNO$_3$. The material was filtered and dried in a fluidized bed dryer, slurried in acetic acid, and packed in a 24 mm I.D. column. A 50 ml portion of acetic acid containing 0.865 wt % MeI was passed through the resin bed at 4-5 ml/min (8-10 bed volumes/hr). Greater than 99.98% of the MeI was removed from the acetic acid.

EXAMPLE V

A 30 ml portion of silver-exchanged strong acid ion exchange resin was prepared by mixing Amberlyst ®15 ion exchange resin with 8.8 g of AgOAc in water until the silver ion was absorbed. A 50 ml buret was charged with a slurry of the silver-exchange resin. Acetic acid containing 17.3 ppm MeI was passed through the column at a flow rate of 14 BV/hr. Samples which were taken after 3, 9, and 15 bed volumes (1 bed volume=30 ml) of acid had been treated contained 1 ppb, 1 ppb, and 5 ppb MeI respectively (removal efficiencies of 99.994%, 99.994%, and 99.97%).

Additional acetic acid containing 104 ppm MeI was allowed to through the used resin bed. Samples taken after 3, 9, and 15 additional bed volumes of acid has been treated contained 1 ppb MeI or less (removal efficiency greater than 99.999%).

Three additional bed volumes of acetic acid containing 0.865 wt % MeI were passed through the column. Greater than 99.98% removal efficiency was observed.

EXAMPLE VI

A 30 ml portion of Amberlyst®15 ion exchange resin was charged as in example 6 with 7.6 g of Hg(OAc)$_2$ and packed into a 50 ml buret. A 50 ml volume of acetic acid was passed through the resin bed at a flow rate of 18 bed volumes per hour (average contact time was ~100 seconds). Greater than 99.99% removal efficiency of MeI was obtained.

EXAMPLE VII

A 2" I.D. column was packed (bottom to top) by pouring into the column acetic acid slurries of 1.0 l granular activated carbon (Pittsburg PCB 12×30), 1.0 l strong-acid ion exchange to catch any silver removed from the silver-exchange resin above (Rohm & Haas Amberlyst®15), 1.0 l of silver-exchanged Amberlyst®15 which had been prepared by mixing 150 g AgOAc with the resin in acetic acid solvent until the silver was absorbed, and 1.0 l of additional PCB 12×30 activated carbon.

Acetic acid containing 50 ppm I as methyl iodide (28 ppm) and HI/I$_2$ (25 ppm HI initially which partially oxidized to I$_2$) was pumped downflow through the column at a flow rate of 2 gallons per hour. Treated acetic acid was collected 55 gallon containers (ca. 410 lbs.). Analyses are tabulated below:

| Total Acid Treated (lb) | Analyses | | Total Iodide Removal Efficiency (%) |
|---|---|---|---|
| | MeI (ppb) | HI/I$_2$ (ppb) | |
| 418 | 9.3 | 4 | 99.97 |
| 832 | 11.2 | 4 | 99.97 |
| 1236 | 47.4 | 5 | 99.90 |

EXAMPLE VIII

Acetic acid containing hexyl iodide was passed at a flow rate of 8.75 ml/min (10.1 bed volumes/hr) through a column consisting of 52 ml of silver-exchanged strong acid ion exchange resin (Amberylst®15), prepared as in example 5 using 6.4 g AgOAc per 52 ml resin. Samples were collected and analyzed throughout the run. Results are tabulated below.

| Cumulative Run Time (hrs) | (hexyl iodide) (ppb) | Removal Efficiency (%) |
|---|---|---|
| Feed | 493000 | — |
| 0.33 | 25 | 99.995 |
| 4.0 | 960 | 99.8 |
| 7.5 | 5120 | 99.0 |
| 9.5 | 16635 | 96.6 |
| 12.0 | 27929 | 94.3 |
| 13.0 | 38576 | 92.2 |

What is claimed is:

1. A method for removing iodide compounds from a non-aqueous organic medium comprising contacting the medium containing said iodide compounds with an ion exchange resin characterized in that the resin is a macroreticulated strong-acid cation exchanged resin which is stable in the organic medium and has at least one percent of its active sites converted to the silver or mercury form.

2. The method of claim 1 wherein the non-aqueous organic medium is acetic acid and from about 25 to about 75 percent of the active sites are in the silver form.

3. The method of claim 2 also comprising contacting said acetic acid with a carbonaceous material prior to contacting the acid with the cation exchange resin.

4. The method of claim 2 wherein the acetic acid contains alkyl iodide.

5. The method of claim 4 wherein the alkyl iodide is selected from the group consisting of methyl iodide, hexyl iodide, and mixtures thereof.

6. The method of claim 5 wherein the acetic acid is contacted with the resin at a flow rate of about 0.5 to about 20 bed volumes per hour at a temperature from about 17° C. to about 100° C.

7. The method of claim 6 wherein the flow rate is about 6 to about 10 bed volumes per hour and the temperature is about 20° C. to about 35° C.

* * * * *

REEXAMINATION CERTIFICATE (2289th)
United States Patent [19]
Hilton

[11] B1 4,615,806

[45] Certificate Issued  May 3, 1994

[54] REMOVAL OF IODIDE COMPOUNDS FROM NON-AQUEOUS ORGANIC MEDIA

[75] Inventor: Charles B. Hilton, Corpus Christi, Tex.

[73] Assignee: American Hoechst Corporation

Reexamination Request:
No. 90/003,078, Jun. 1, 1993

Reexamination Certificate for:
Patent No.: 4,615,806
Issued: Oct. 7, 1986
Appl. No.: 708,992
Filed: Mar. 7, 1985

[51] Int. Cl.$^5$ .............................. B01D 15/04
[52] U.S. Cl. .................... 210/690; 562/608

[56] References Cited

U.S. PATENT DOCUMENTS

| | | | |
|---|---|---|---|
| 3,630,681 | 12/1971 | Arikawa | 23/230 |
| 3,732,320 | 5/1973 | Ford | 260/637 R |
| 3,772,156 | 11/1973 | Johnson et al. | 203/33 |
| 3,943,229 | 3/1976 | Keener et al. | 423/240 |
| 4,007,130 | 2/1977 | Leach | 252/411 R |
| 4,113,754 | 9/1978 | Kummer et al. | 260/429 R |
| 4,305,882 | 12/1981 | Emken et al. | 260/428.5 |
| 4,410,449 | 10/1983 | Diessel et al. | 502/24 |
| 5,139,981 | 8/1992 | Kurland | 502/11 |
| 5,227,524 | 7/1993 | Jones | 562/608 |

FOREIGN PATENT DOCUMENTS

| | | |
|---|---|---|
| 1808156 | 6/1970 | Fed. Rep. of Germany . |
| 1598589 | 5/1972 | Fed. Rep. of Germany . |
| 1253607 | 11/1971 | United Kingdom . |
| 2112394 | 7/1983 | United Kingdom . |

OTHER PUBLICATIONS

Nikolsk et al., "Ionites (ion exchange resins) in Chemical Technology," *Chemistry*, Leningrad Editions (1982) (English translation).

Owens, "Chemical Processing by Ion Exchange," Rohm & Haas Company (Jun. 1980).

Kunin, "Two Decades of Macrorecticular ion Exchange Resins," *Amber-hi-lites*, Rohm & Haas Company (1979).

Samuelson, Chapter 7, "Non-Aqueous Solutions," *Ion Exchange Separations in Analytical Chemistry*, John Wiley & Sons (1963).

"Amberlyst 15 Synthetic Resin Catalyst," Rohm & Haas Company (Dec. 1976).

"Ion Exchange in Non-Aqueous Media with Amberlyst ® Resins," Rohm & Haas Company (undated).

Kunin et al., "Macroreticular Ion Exchange Resins," *Amber-Hi-Lites*, Rohm & Haas Company, No. 78 (Nov. 1963).

Khan et al., "Studies on Removal of Methyl Iodide by Activated Charcoal," Government of India Atomic Energy Commission (1975).

S. B. Hingorani & K.S. Venkateswerlu, Chem. Eng. World, vol. XII, No. 5, "Removal of Radioactive Iodine and Methyl Iodide by use of Silver-Impregnated Resin", pp. 59-61, May 1977.

Amber-hi-lites, No. 126, Rohm & Haas Company, "Ion Exchange in Non-Aqueous Media", Philadelphia, Pa., Jan. 1972.

Gould, E. S., "Mechanism and Structure in Organic Chemistry", Holt, Rinehart and Winston, New York (1959), pp. 272-274; 292-303.

"Rodd's Chemistry of Carbon Compounds" Elsevier Publishing Company, Amsterdam (1964), pp. 278.

Hendrickson et al, "Organic Chemistry", McGraw-Hill, New York (1970), pp. 388.

*Primary Examiner*—Ivars Cintins

[57] ABSTRACT

The invention relates to a method for removing iodide compounds from a non-aqueous organic medium, such as acetic acid. The medium is contacted with a macroreticulated strong-acid cation exchange resin which is stable in the organic medium and has at least one percent of its active sites converted to the silver or mercury form.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-7 is confirmed.

* * * * * ic
REEXAMINATION CERTIFICATE (2998th)

United States Patent [19]
Hilton

[11] B2 4,615,806
[45] Certificate Issued Sep. 17, 1996

[54] REMOVAL OF IODIDE COMPOUNDS FROM NON-AQUEOUS ORGANIC MEDIA

[75] Inventor: Charles B. Hilton, Corpus Christi, Tex.

[73] Assignee: American Hoechst Corp., New York, N.Y.

Reexamination Requests:
No. 90/003,792, Apr. 12, 1995
No. 90/004,166, Mar. 4, 1996

Reexamination Certificate for:
Patent No.: 4,615,806
Issued: Oct. 7, 1996
Appl. No.: 708,992
Filed: Mar. 7, 1985

Reexamination Certificate B1 4,615,806 issued May 3, 1994

[51] Int. Cl.$^6$ .................................................... B01D 15/04
[52] U.S. Cl. ........................................... 210/690; 562/608

[56] References Cited

U.S. PATENT DOCUMENTS

3,409,691  11/1968  Small et al. ............................. 260/676
4,007,130  2/1977  Leach et al. .......................... 252/411 R

FOREIGN PATENT DOCUMENTS

2112394  7/1983  United Kingdom .

OTHER PUBLICATIONS

Hingorani et al. *Chem. Eng. World*, vol. XII, No. 5, May 1977.
*amber–hi–lites*, "Ion Exchange in Non–Aqueous Media", Rohm & Haas Company, No. 126, Jan. 1972.
Rohm & Haas technical bulletin, "Ion Exchange Non–Aqueous Media with Amberlyst® Resins".
Kunin, *Ion Exchange Resins*, Huntington, N.Y.: Krieger Publishing, 1972.
*Chemical Abstracts*, 87, 190882f (1977).
Gould, *Mechanism and Structure in Organic Chemistry*, New York: Holt, Rinehart and Winston, 1972.
Streitwieser, *Chemical Reviews*, vol. 56 (4), Aug. 1956.
Bunton, *Nucleophilic Substitution at a Saturated Carbon Atom*, New York: Elsevier, 1963.
Rudakov et al, *Russian Chemical Reviews*, 43 (4), 1974.
Finar, *Organic Chemistry*, vol. 1, Sixth Ed., London: Longman, 1973.
Weast, *Handbook of Chemistry & Physics*, 63d Ed., 1982–1983.
Rudakov et al, *Reakts. sposobn. organ. soedyn.* 9, 31 (1972), "Kinetics and Mechanism of Hydrolysis of Methyl Iodide Influence by Silver Ions".
Colcleugh, D. W. and Moelwyn–Hughes, "The Kinetics of the Reaction of Methyl Iodide with Silver nitrate and Silver Perchlorate in Aqueous Solution", *J. Chem. Soc.*, 2542–2545 (1964).
Redies, W. F. et al, *J. Phys. Chem.*, 48, 224–230 (1944).
A Study of Fission Product Uptake By Selection Ion Loaded Organic Exchange Resin. A Thesis submitted to the University of Bombay for the Degree of Doctor of Philosphy in Chemistry, by S. B. Hingorani, Air Monitoring Section, Division of Radiological Protection, Shabha Atomic Research Center, Bombay, 1979.

*Primary Examiner*—Ivars C. Cintins

[57] ABSTRACT

The invention relates to a method for removing iodide compounds from a non-aqueous organic medium, such as acetic acid. The medium is contacted with a macroreticulated strong-acid cation exchange resin which is stable in the organic medium and has at least one percent of its active sites converted to the silver or mercury form.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-7 is confirmed.

* * * * *